United States Patent
Danger et al.

(10) Patent No.: US 6,896,679 B2
(45) Date of Patent: May 24, 2005

(54) SURGICAL SAW BLADE COMPRISING RECESSES IN THE WORKING AREA

(75) Inventors: Karl-Heinz Danger, Detmold (DE); Michael Küllmer, Lemgo (DE)

(73) Assignee: Gebr, Brassler GmbH & Co. KG, Lemgo (DE)

( * ) Notice: Subject to any disclaimer, the term of this patent is extended or adjusted under 35 U.S.C. 154(b) by 340 days.

(21) Appl. No.: 10/097,466

(22) Filed: Mar. 14, 2002

(65) Prior Publication Data

US 2002/0133185 A1 Sep. 19, 2002

(30) Foreign Application Priority Data

Mar. 14, 2001 (DE) .......................................... 101 12 288

(51) Int. Cl.[7] .............................................. A61B 17/14
(52) U.S. Cl. .......................................... 606/82; 606/178
(58) Field of Search .............................. 606/79, 82, 85, 606/167, 171, 176, 177, 178, 179, 180; 30/346, 346.1, 351; 83/697, 835–855

(56) References Cited

U.S. PATENT DOCUMENTS

| 213,439 A | * | 3/1879 | Miller .......................... 83/835 |
| 4,036,236 A | | 7/1977 | Rhodes, Jr. |
| 4,393,590 A | * | 7/1983 | Pantzar ......................... 30/387 |
| 4,442,559 A | * | 4/1984 | Collins ........................... 7/158 |
| 4,513,742 A | | 4/1985 | Arnegger |
| 4,584,999 A | | 4/1986 | Arnegger |
| 4,718,398 A | * | 1/1988 | Hallez .......................... 125/15 |
| 5,306,285 A | | 4/1994 | Miller et al. ................. 606/177 |
| 5,735,866 A | * | 4/1998 | Adams et al. ............... 606/178 |

FOREIGN PATENT DOCUMENTS

| DE | 3222339 A1 | 1/1983 |
| DE | 19804762 A1 | 7/1999 |
| DE | 100 10 526 A 1 | 10/2001 |
| EP | 0 695 607 A1 | 2/1996 |
| GB | 2 103 148 A | 4/1983 |

* cited by examiner

Primary Examiner—David O. Reip
(74) Attorney, Agent, or Firm—Thompson Coburn LLP

(57) ABSTRACT

The present invention relates to a surgical saw blade comprising a clamping portion and a working area provided with a toothing, wherein a plurality of recesses are formed in the working area.

13 Claims, 2 Drawing Sheets

SURGICAL SAW BLADE COMPRISING RECESSES IN THE WORKING AREA

BACKGROUND OF THE INVENTION

The present invention relates to a surgical saw blade comprising a clamping portion and a working area provided with a toothing. Surgical saw blades of the described type are known from the prior art in many different designs. They are mounted on a drive unit by which they can be induced to perform an oscillating reciprocating movement. It is thereby possible to carry out, for instance, precise bone cuts. The saw blades can be guided manually, but it is also possible to use the blades together with templates to produce precise predetermined cuts.

As a result of the planar design of the saw blades, these conceal the working area during specific operations, so that it is difficult or even impossible to monitor the sawing operation optically. That is why it has already been suggested that the working area should be provided with a large recess so that the toothing is only connected via lateral edge portions to the clamping portion. Such constructions, however, are very unstable and do not provide the necessary strength and stability. Further, an exact guidance of the cutting operation is not possible.

BRIEF SUMMARY OF THE INVENTION

It is the object of the present invention to provide a surgical saw blade of the above-mentioned type which, while being of a simple structure and producible at low costs, permits an optical monitoring of the cutting operation and is characterized by high stability and strength.

According to the invention this object is achieved by the features of the independent claim; the dependent claims show further advantageous developments of the invention.

Thus, according to the invention a plurality of recesses are formed in the working area.

The saw blade according to the invention is characterized by a number of considerable advantages. Thanks to the plurality of recesses, the mechanical strength of the saw blade is not impaired. Rather, as will be further explained herein, the strength is additionally enhanced thereby. Due to the oscillating movement of the saw blade, the ability to optically monitor the working area is greatly improved through the plurality of small recesses and to carry out the operation itself in a controlled manner.

It is particularly advantageous when the recesses are arranged in the form of a honeycomb structure. Such a geometrical shape ensures a high degree of strength and stability while only requiring a minimum amount of material.

The honeycomb structure is preferably designed such that it comprises recesses defined by webs. The recesses may be hexagonal, rectangular or round or may be provided with any other geometrical shape.

It is particularly advantageous when the recesses extend substantially over the whole width of the working area so that concealment of the working area of the saw blade is minimized.

Since it may be particularly important to monitor the cutting portion of the saw blade directly during the sawing operation, the recesses may extend from the toothing.

Furthermore, it may be advantageous to provide the recesses over a substantial part of the length of the working area to keep the invisible portion as small as possible.

Furthermore, it may be particularly advantageous with respect to a maximum mechanical strength of the saw blade when the recesses are arranged in symmetry with a center axis of the saw blade.

BRIEF DESCRIPTION OF THE SEVERAL VIEWS OF THE DRAWINGS

The accompanying drawings, which are incorporated in and form a part of the specification, illustrate the embodiments of the present invention and together with the description, serve to explain the principles of the invention. In the figures, like parts are provided with like reference numerals. In the drawings.

DETAILED DESCRIPTION OF THE INVENTION

Figures 1, 2:
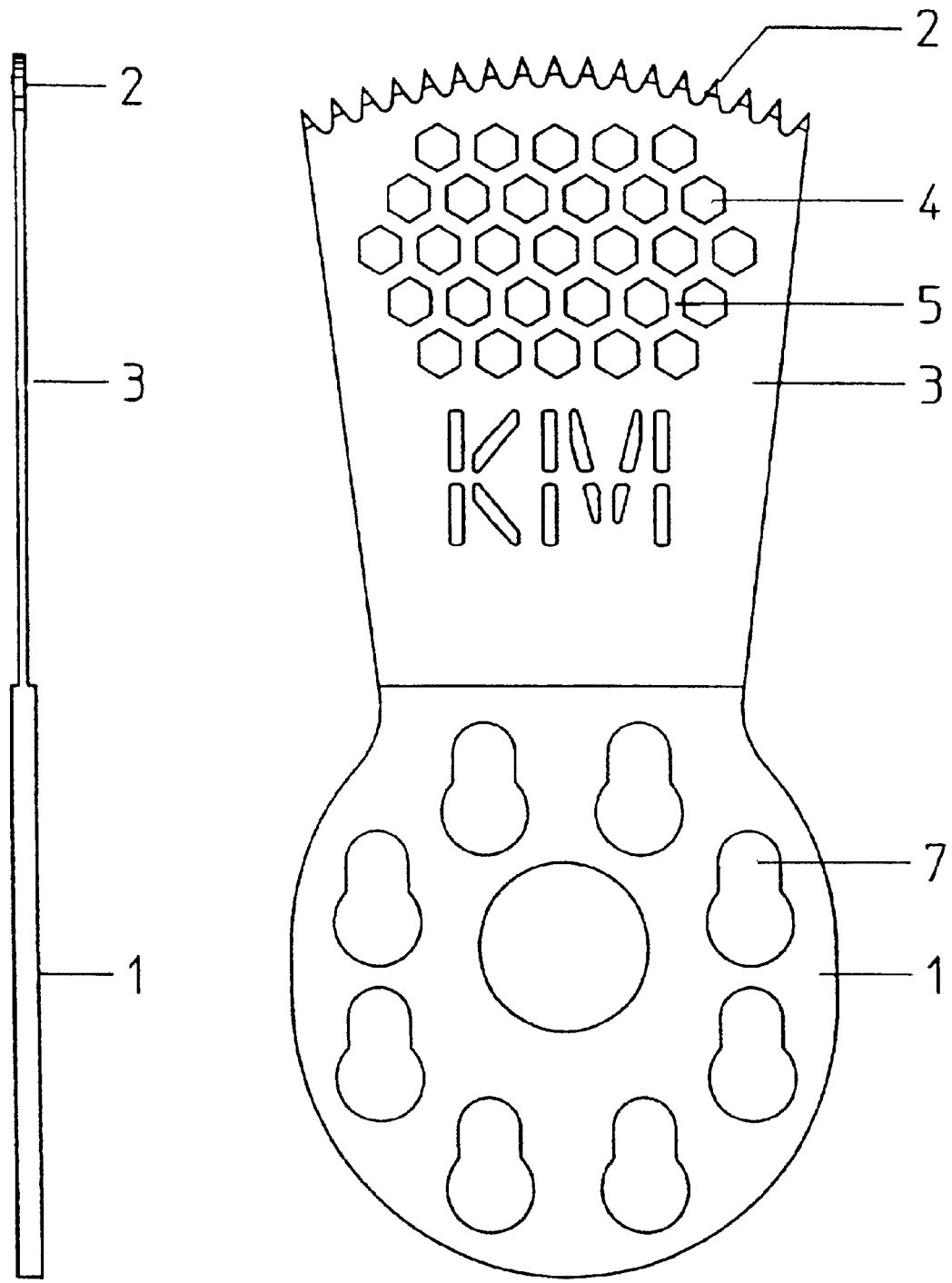
FIG. 1 is a top plan view of a first embodiment of the saw blade according to the invention.
FIG. 2 is a side view of the saw blade shown in FIG. 1.

As can be seen in FIG. 1, the saw blade comprises a substantially circular clamping portion 1 which is provided with a plurality of mounting openings 7. Both the mounting openings and the dimension of the clamping portion 1 are known from the prior art, so that a detailed description is omitted. In one embodiment, the diameter of the clamping portion 1 is approximately 16 mm.

The clamping portion is followed by a working area 3 whose front arcuate edge is provided with a toothing 2, the center point of the arc preferably being positioned in the center of rotation or pivotal point of the saw blade. In one embodiment, toothing 2 may have a width of approximately 15 mm and the total length of the saw blade may be approximately 35 mm.

A plurality of hexagonal recesses that are arranged in honeycomb-like fashion are formed in the working area 3, the recesses 4 being separated from one another by webs 5. The honeycomb structure shows a high degree of strength, so that the total strength of the saw blade, as compared to a working area without recesses, is virtually not reduced.

As becomes apparent from the side view of FIG. 2, the working area 3 has a smaller thickness than the clamping portion 1 and the toothing 2.

Figures 3, 4:
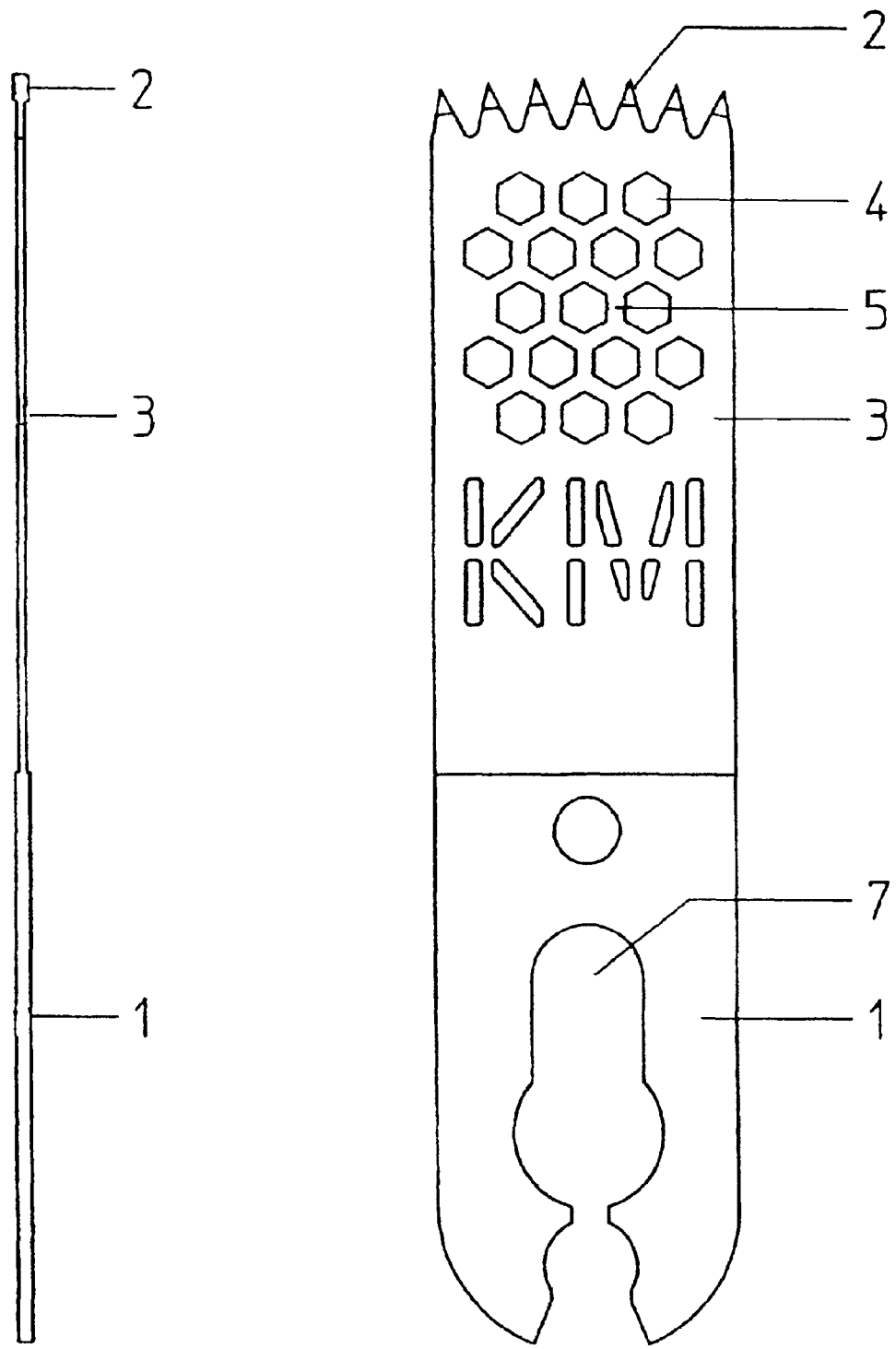
FIG. 3 is a top plan view of a further embodiment of a saw blade according to the invention.
FIG. 4 is a side view of the saw blade shown in FIG. 3.

FIGS. 3 and 4 show a further embodiment in which both the clamping portion 1 and the working area 3 are defined by parallel outer edges, resulting in a substantially strip-like contour of the saw blade. In this embodiment, too, the toothing 2 is arranged in arcuate fashion, the center point of the arc of the toothing 2 preferably being positioned, like in the embodiment of FIG. 1, in the center of rotation or pivotal point of the saw blade.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

We claim:

1. A surgical saw blade comprising:

a clamping portion adjacent a proximal end; and a working area adjacent a distal end, said working area comprising an arcuate edge having integral saw teeth and a plurality of throughholes formed therein; wherever the throughholes are arranged in the form of a honeycomb structure.

2. The surgical saw blade according to claim 1, wherein said honeycomb structure comprises said recesses and a plurality of webs defined thereby.

3. The surgical saw blade according to claim 1, wherein said recesses are substantially hexagonal.

4. The saw blade according to claim 1, wherein said recesses are substantially rectangular.

5. The saw blade according to claim 1, wherein said recesses are substantially round.

6. The saw blade according to claim 1, wherein said recesses are substantially triangular.

7. The saw blade according to claim 1, wherein said recesses are substantially arranged across the width of said working area.

8. The saw blade according to claim 1, wherein said recesses extend from said toothing.

9. The saw blade according to claim 1, wherein said recesses extend from said toothing over a substantial part of said working area.

10. The saw blade according to claim 1, wherein said recesses are arranged in symmetry with a center axis of said saw blade.

11. The surgical saw blade according to claim 1, wherein the clamping portion includes at least one mounting opening, the mounting opening being adapted to engage a drive unit to mount the saw blade on the drive unit; and wherein the working area extends from the clamping portion and the plurality of recesses are arranged such that at least one of the plurality of recesses is surrounded by at least six other recesses.

12. The surgical saw blade of claim 1, wherein the clamping portion includes at least one mounting opening, the mounting opening being adapted to engage a drive unit to mount the saw blade on the drive unit; and wherein the working area extends from the clamping portion and the working area has a plurality of webs defining the plurality of recesses, the plurality of recesses arranged in rows, the rows configured such that adjacent rows are offset from each other to form the honeycomb structure, the adjacent rows being offset by an amount equal to substantially one half of a diameter of a recess.

13. The surgical saw blade of claim 1, wherein the clamping portion includes at least one mounting opening, the mounting opening being adapted to engage a drive unit to mount the saw blade on the drive unit; and wherein the working area extends from the clamping portion and the working area has a plurality of webs defining the plurality of recesses, the plurality of recesses arranged in rows, the rows being configured such that alternating rows are aligned with each other.

* * * * *